(12) United States Patent
Tamura

(10) Patent No.: US 8,343,054 B1
(45) Date of Patent: Jan. 1, 2013

(54) METHODS AND APPARATUS FOR ULTRASOUND IMAGING

(75) Inventor: Tadashi Tamura, North Haven, CT (US)

(73) Assignee: Hitachi Aloka Medical, Ltd., Tokyo (JP)

( * ) Notice: Subject to any disclaimer, the term of this patent is extended or adjusted under 35 U.S.C. 154(b) by 57 days.

(21) Appl. No.: 13/079,456

(22) Filed: Apr. 4, 2011

Related U.S. Application Data

(60) Provisional application No. 61/388,097, filed on Sep. 30, 2010.

(51) Int. Cl.
*A61B 8/00* (2006.01)
(52) U.S. Cl. ......... 600/447; 600/437; 600/441; 600/443
(58) Field of Classification Search ........... 600/437–469
See application file for complete search history.

(56) References Cited

U.S. PATENT DOCUMENTS

| | | | |
|---|---|---|---|
| 6,423,004 B1 | 7/2002 | Dong et al. | |
| 6,547,732 B2 * | 4/2003 | Jago | 600/437 |
| 6,719,693 B2 * | 4/2004 | Richard | 600/437 |
| 6,843,770 B2 | 1/2005 | Sumanaweera | |
| 7,600,689 B2 * | 10/2009 | Tsikos et al. | 235/462.43 |
| 7,819,805 B2 * | 10/2010 | Davies et al. | 600/437 |
| 7,850,611 B2 * | 12/2010 | Davies et al. | 600/447 |
| 2001/0014773 A1 * | 8/2001 | Jago | 600/437 |
| 2003/0187357 A1 * | 10/2003 | Richard | 600/437 |
| 2004/0077946 A1 * | 4/2004 | Ohmiya | 600/437 |

OTHER PUBLICATIONS

M. Berson et al., "Compound Scanning With an Electrically Steered Beam", Ultrasonic Imaging, vol. 3, Issue 3, Jul. 1981, (pp. 303-308, total 6 pages).

* cited by examiner

*Primary Examiner* — Sanjay Cattungal
(74) *Attorney, Agent, or Firm* — Buckley, Maschoff & Talwalkar LLC

(57) ABSTRACT

Systems and methods are described to create a plurality of ultrasound images of an area, each of the plurality of ultrasound images acquired using a respective beam steering angle, determine, for each of a plurality of image pixel locations in each of the plurality of ultrasound images, a value of an image pixel located at an image pixel location, identify, for each of the plurality of image pixel locations, a value among the plurality of values determined for the pixel location other than the largest value of the plurality of values determined for the pixel location, and create a first output image in which each of the plurality of image pixel locations of the output image includes an image pixel having the value identified for the image pixel location.

12 Claims, 7 Drawing Sheets

METHODS AND APPARATUS FOR ULTRASOUND IMAGING

CROSS-REFERENCE TO RELATED APPLICATION

The present application claims priority to U.S. Provisional Patent Application Ser. No. 61/388,097, filed on Sep. 30, 2010 and entitled "Method and Apparatus for Ultrasound Imaging", the contents of which are incorporated herein by reference for all purposes.

BACKGROUND

Systems and methods described herein generally relate to the field of medical ultrasound imaging. More specifically, embodiments described below relate to methods and systems which may be employed to generate images of interventional devices such as biopsy needles.

Conventional ultrasound imaging may be used to produce images of internal biological tissue structures. These images may be used to detect and diagnose internal abnormalities, to assist in medical interventions (e.g., real-time viewing of a needle during a biopsy procedure), or for any other purpose. Under many conditions, conventional ultrasound imaging produces images which are suitable for their intended purpose. However, under certain conditions and/or for certain purposes, images produced by conventional ultrasound imaging are not satisfactory.

FIG. 1 illustrates ultrasound imaging of a medical intervention. The area 150 includes internal tissue and a target lesion 140. During a biopsy, the biopsy needle 120 is inserted into the tissue from the skin surface to the target lesion 140 and under the ultrasound transducer 110. The needle 120 is therefore tilted with respect to the skin surface and the transducer 110.

To acquire a B-mode image, ultrasound beams are transmitted directly downward from the transducer 110 with no beam steering (0 degrees) and resulting ultrasound beams are then received by the transducer 110. Although only one ultrasound beam 170 is shown in FIG. 1, multiple ultrasound beams (e.g., a few hundred) may be transmitted. A B-mode image 150 may then be created based on the received beams using known techniques.

The reflectivity of the needle at the illustrated entry angle is lower than the reflectivity of the needle if entering parallel to the transducer 110. Therefore, as shown in FIG. 1, an ultrasound image of the needle 130 will appear faint in the resulting B-mode image 150. As a result, it is difficult to guide the biopsy based on the B-mode image 150.

DETAILED DESCRIPTION

Embodiments will be described with reference to the accompanying drawing figures wherein like numbers represent like elements throughout. Before embodiments are explained in detail, it is to be understood that embodiments are not limited in their application to the details of the examples set forth in the following description or illustrated in the figures. Other embodiments may be practiced or carried out in a variety of applications and in various ways. Also, it is to be understood that the phraseology and terminology used herein is for the purpose of description and should not be regarded as limiting. The use of "including," "comprising," or "having," and variations thereof herein is meant to encompass the items listed thereafter and equivalents thereof as well as additional items. The terms "mounted," "connected," and "coupled," are used broadly and encompass both direct and indirect mounting, connecting, and coupling. Further, "connected," and "coupled" are not restricted to physical or mechanical connections or couplings.

Figure 1:
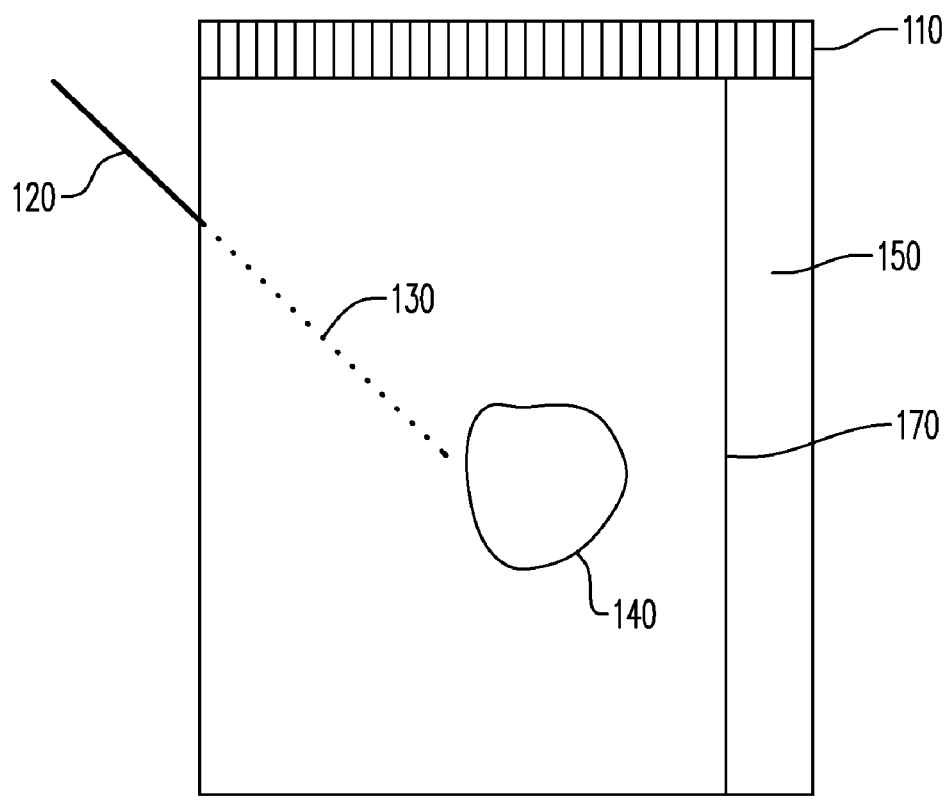
FIG. 1. A conventional ultrasound image of a biopsy needle.

According to the convention used herein, an ultrasound beam steering angle of 0 degrees refers to a beam which proceeds perpendicularly from the transducer array (e.g., with reference to FIG. 1, vertically from the transducer to the bottom of the image). A beam steering angle of 20 degrees refers to a beam steered 20 degrees to the left of a 0 degree beam, while a beam steering angle of -20 degrees refers to a beam steered 20 degrees to the right of the 0 degree beam.

Figure 2A:
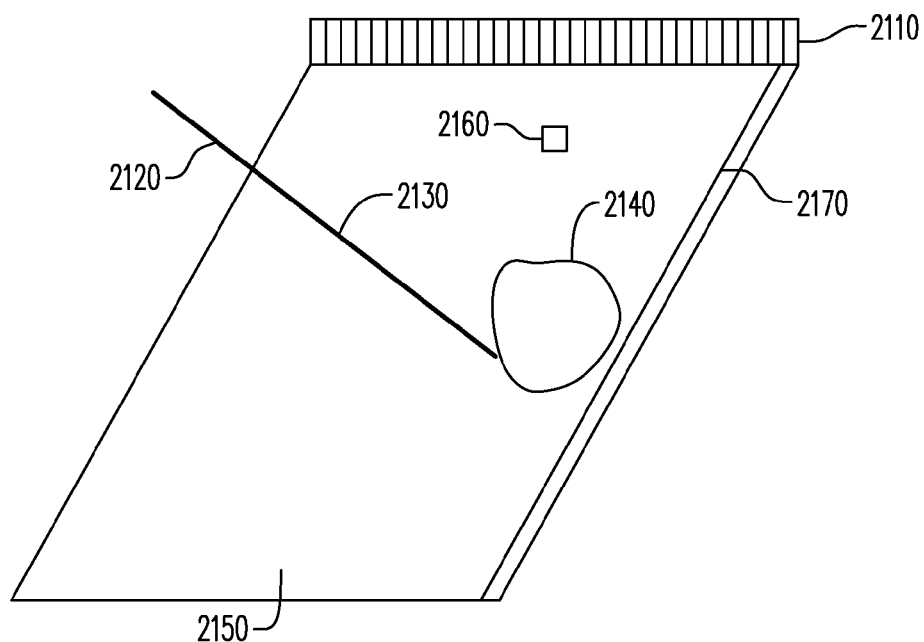
FIG. 2A. An ultrasound image acquired using a beam steering angle (e.g., 20 degrees).
Figure 2B:
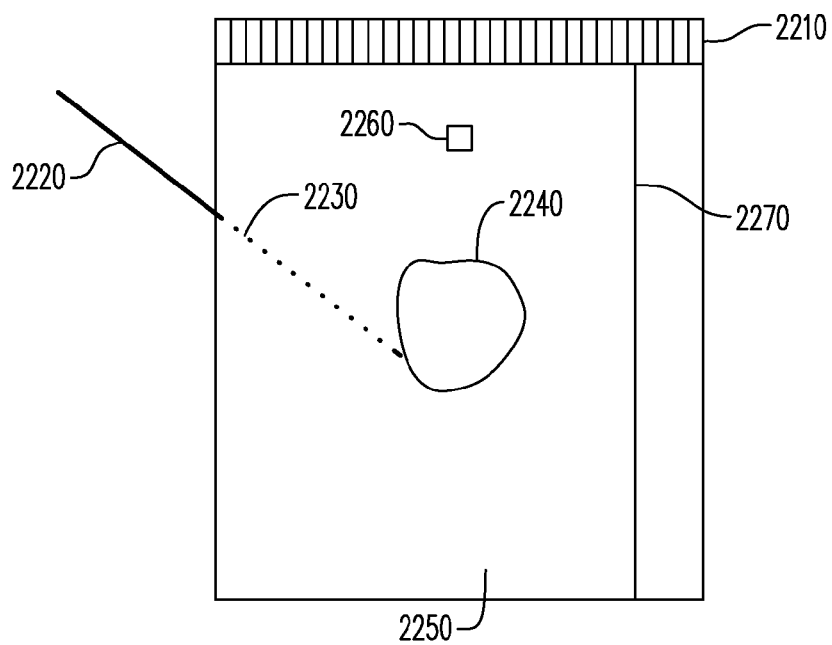
FIG. 2B. An ultrasound image acquired using no beam steering angle (e.g., 0 degrees)

FIG. 2A shows an ultrasound image of tissue area 2150 including a biopsy needle 2120 and a target lesion 2140. An ultrasound image of area 2150 is acquired using an ultrasound transducer 2110 comprising an array of elements and an ultrasound beam transmitted from the transducer array at a beam steering angle of, e.g., 20 degrees to the left. One ultrasound beam 2170 is shown as an example although multiple ultrasound beams (e.g. a few hundred) may be used to acquire the image. Since the ultrasound beams are steered to the left and the angle between the ultrasound beams and the needle axis is close to 90 degrees, the needle 2130 reflects the ultrasound beam fairly well. Accordingly, the needle 2130 may be more visible in the resulting image 2150 of FIG. 2A than a needle image 2230 in the ultrasound image 2250, acquired using no beam steering angle, and depicted in FIG. 2B.

Figure 2C:
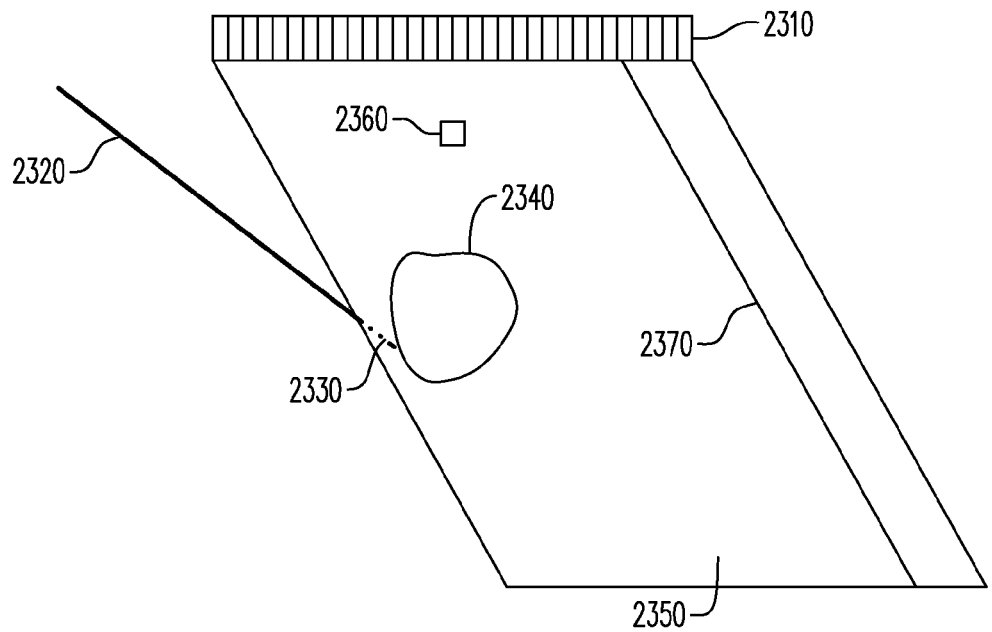
FIG. 2C. An ultrasound image acquired using a beam steering angle (e.g., -20 degrees).

FIG. 2C shows an ultrasound image of tissue area 2350 including a biopsy needle 2330 and a target lesion 2340, acquired at a beam steering angle of e.g., -20 degrees to the right. One ultrasound beam 2370 is shown as an example although multiple ultrasound beams (e.g. a few hundred) may be used to acquire an image. Due to the small angle at which the ultrasound beams intersect the needle, the needle does not reflect the transmitted ultrasound beams as well as in the case of 20 degree beam steering angle shown in FIG. 2A. As a result, an ultrasound image of the needle 2230 will be fainter than the ultrasound image of the needle 2130 shown in FIG. 2A, and perhaps invisible.

Figure 2D:
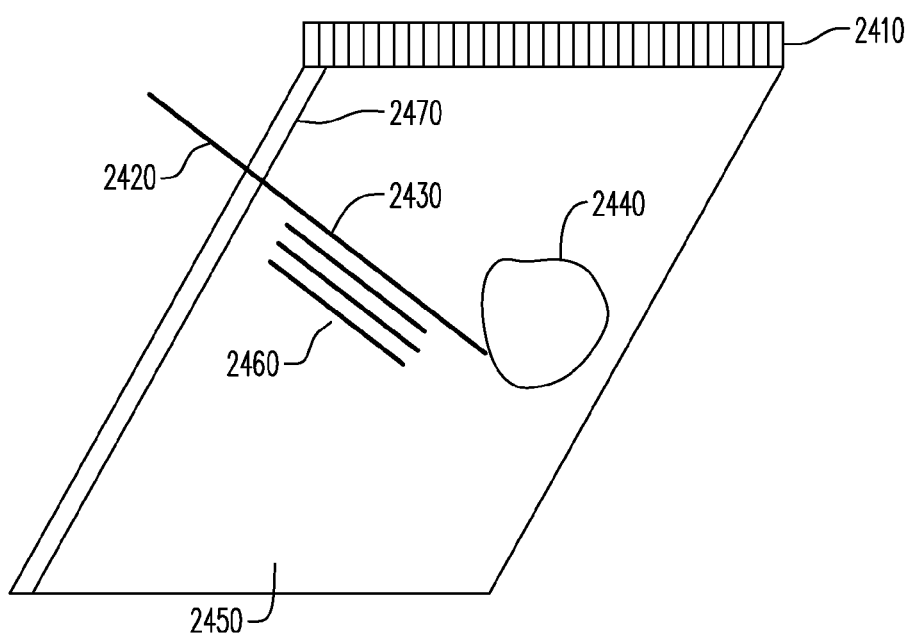
FIG. 2D. An ultrasound image acquired using ultrasound beams intersecting a biopsy needle at near 90 degrees, showing reverberation noise at a lower side of the needle.
Figure 2E:
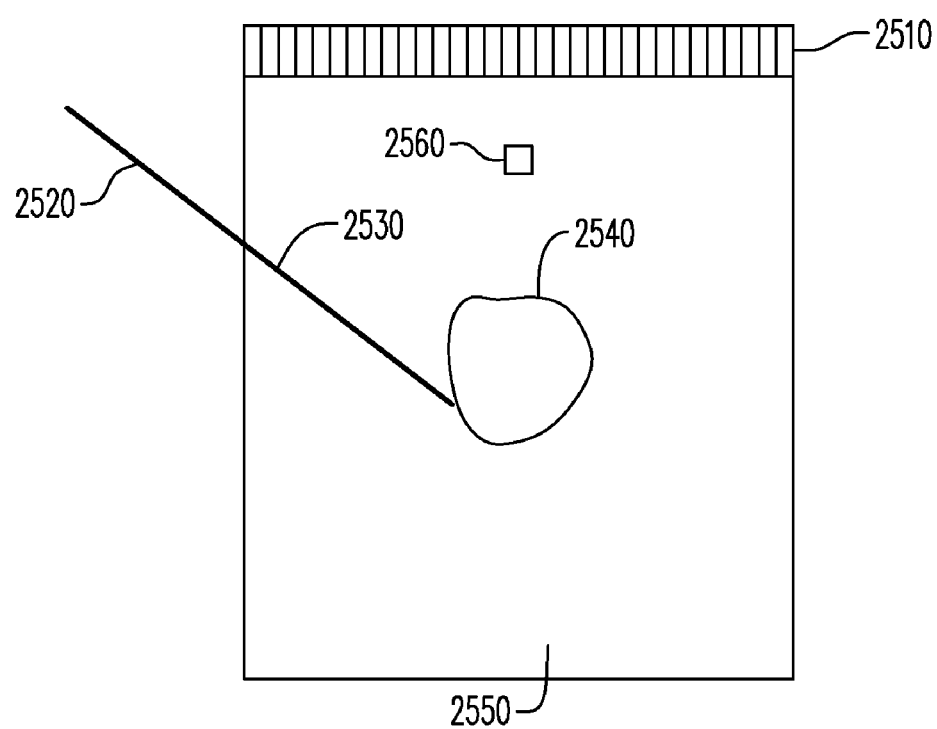
FIG. 2E. A first output ultrasound image of a biopsy needle according to some embodiments.

Some embodiments operate to create a single image based on multiple ultrasound images acquired using different beam steering angles. Generally, for every image pixel location, a value among the multiple images is selected to create a first output image 2550 as shown in FIG. 2E. For example, a value of an image pixel at an image pixel location 2160 in FIG. 2A is compared with values of the image pixels at the same pixel location 2260 of FIG. 2B, and at the same pixel location 2360 of FIG. 2C. Of the multiple values, it may be contemplated to identify a largest value for this image pixel location and use this largest value for the value of the first output image at image pixel location 2560 in FIG. 2E. The present inventor has discovered that, under some conditions, ultrasound signals received from a biopsy needle may be too large due to the intersecting ultrasound beam being too close to the 90-degree angle to the needle axis and may therefore create reverberation noise 2460 at the lower side of a biopsy needle in the resulting image as shown in FIG. 2D.

Accordingly, in some embodiments, the identified value for an image pixel location is one of the multiple values for the image pixel location which is not the largest of the multiple values for the image pixel location. Such identification may provide an improved image. Therefore, for a given image pixel location, a second-largest value of the multiple values may be identified for the image pixel location, and may be used for the value of the first output image at image pixel location 2560 in FIG. 2E. In some embodiments, a third-largest value, fourth-largest value, fifth-largest value, sixth-largest value, etc. of the multiple values may be identified for an image pixel location. This processing may be performed for every image pixel location of the first output image 2550. In some embodiment, the multiple images might not include an ultrasound image acquired at a zero degree beam steering angle.

A first output image is therefore created by identifying a value for each image pixel location of the first output image using the method described above. In the example discussed previously, several beam steering angles were used to describe the embodiments. However, the number of beam steering angles may be any number, e.g. 5, 10 or any number. Also the beam steering angle may be varied at a fixed angular increment or at a variable angular increment, or may be selected from a set of beam steering angles.

An image pixel may be the smallest element of an image, and an image may consist of 800×600 pixels, 1024×768 pixels, or any other arrangement.

In some embodiment, the first output image $I_{1,x,y}$ acquired as described previously may be further combined with an ultrasound image $I_{2,x,y}$ acquired at a beam steering angle substantially perpendicular to the ultrasound transducer array (e.g., zero (0) degrees or another small beam steering angle) to create a second output image $I_{x,y}$ because such an ultrasound image $I_{2,x,y}$ exhibits better image quality than the first output image $I_{1,x,y}$ in areas other than the biopsy needle, and exhibits a wider image field. The first output image $I_{1,x,y}$ and the image $I_{2,x,y}$ may be summed using weights.

$$I_{x,y} = w_{1,x,y} \cdot I_{1,x,y} + w_{2,x,y} \cdot I_{2,x,y},$$

where $w_{1,x,y}$ and $w_{2,x,y}$ are fixed values and may be identical to or different from one another.

Furthermore, the weights may depend on image values at each image pixel location as follows, $$w_{1,x,y} = f(I_{1,x,y}, I_{2,x,y})$$

$$w_{2,x,y} = g(I_{1,x,y}, I_{2,x,y})$$

where $w_{1,x,y}$ is a weight of the first output image at (x, y), while $w_{2,x,y}$ is a weight of the ultrasound image with no beam steering at (x, y). $f(I_{1,x,y}, I_{2,x,y})$ and $g(I_{1,x,y}, I_{2,x,y})$ are functions of $I_{1,x,y}$ and $I_{2,x,y}$ (i.e., image values at (x, y) of the first output image and the second image acquired at a beam steering angle substantially perpendicular to the ultrasound transducer array).

In the preceding paragraphs, an example of several beam steering angles is used to illustrate a method according to some embodiments. However, the number of beam steering angles and images may be any number, e.g., 5, 10 or other numbers. Also, the beam steering angles may be other than 20 degrees and may vary from 0 degrees to 90 degrees to the left or 0 degrees to −90 degrees to the right.

Figure 3:
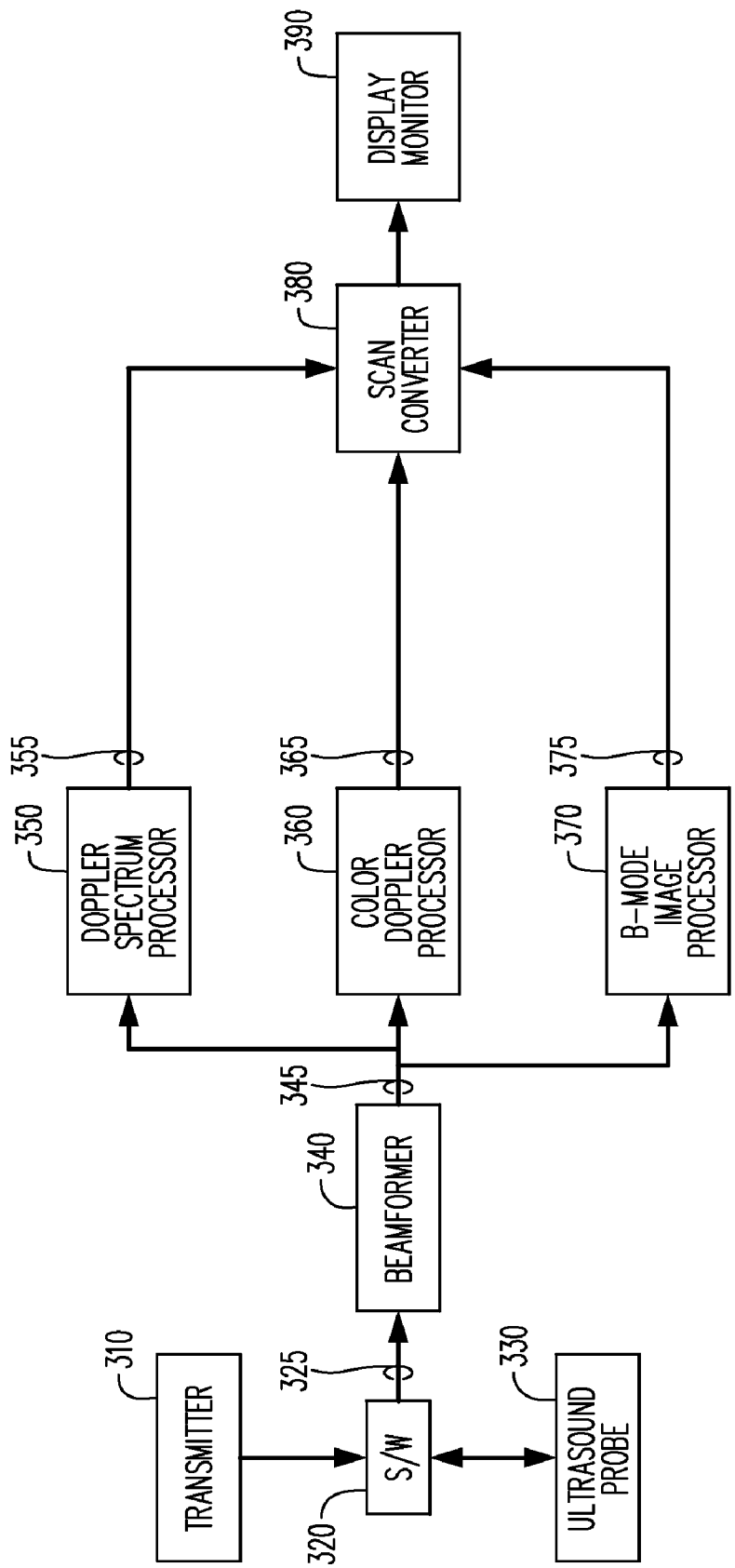
FIG. 3. A diagram of a conventional ultrasound imaging system.

FIG. 3 shows a diagram of a conventional ultrasound diagnostic imaging system with B-mode imaging, Doppler spectrum and color Doppler imaging. The system may include other imaging modes, e.g. elasticity imaging, 3D imaging, real-time 3D imaging, tissue Doppler imaging, tissue harmonic imaging, contrast imaging and others. An ultrasound signal is transmitted from an ultrasound probe 330 driven by a transmitter/transmit beamformer 310 through a transmit/receive switch 320. The probe 320 may consist of an array of transducer elements which are separately driven by the transmitter/transmit beamformer 310 with different time-delays so that a transmit ultrasound beam is focused and steered in tissue. The transmitted ultrasound beam (or signal) is scattered by the tissue and scattered ultrasound signals are returned to the probe 330. The probe then receives the ultrasound signals from the tissue and a receive beamformer 340 receives the received ultrasound signals from the probe 330 through the switch 320 and processes the signals 325. The receive beamformer 340 applies delays and/or phases to the signals 325 and the resultant signals are summed for focusing and steering a receive ultrasound beam. The receive beamformer 340 may also apply apodization, amplification and filtering.

The processed signal 345 is coupled to a Doppler spectrum processor 350, a color Doppler processor 360, and a B-mode image processor 370. The Doppler spectrum processor 350 includes a Doppler signal processor and a spectrum analyzer, and processes Doppler flow velocity signals and calculates and outputs a Doppler spectrum 355. The color Doppler processor 360 processes the received signal 345 and calculates and outputs velocity, power and variance signals 365. The B-mode image processor 370 processes the received signal 345 and calculates and outputs a B-mode image 375 or the amplitude of the signal by amplitude detection.

The Doppler spectrum signals 355, color Doppler processor signals (velocity, power, and variance) 365 and B-mode processor signals 375 are coupled to a scan converter 380 that converts the signals to scan-converted signals. For the B-mode signals, the data from the B-mode image processor 375 are line data which consist of processed beam signals for each receive ultrasound beam and may not have signals for all image pixels with the correct vertical-to-horizontal distance relationship for the display. The scan converter 380 interpolates the line data in two dimensions (x, y) and fills in all image pixels with ultrasound image data. The output of the scan converter 380 is coupled to a display monitor 390 for displaying ultrasound images.

Figure 4:
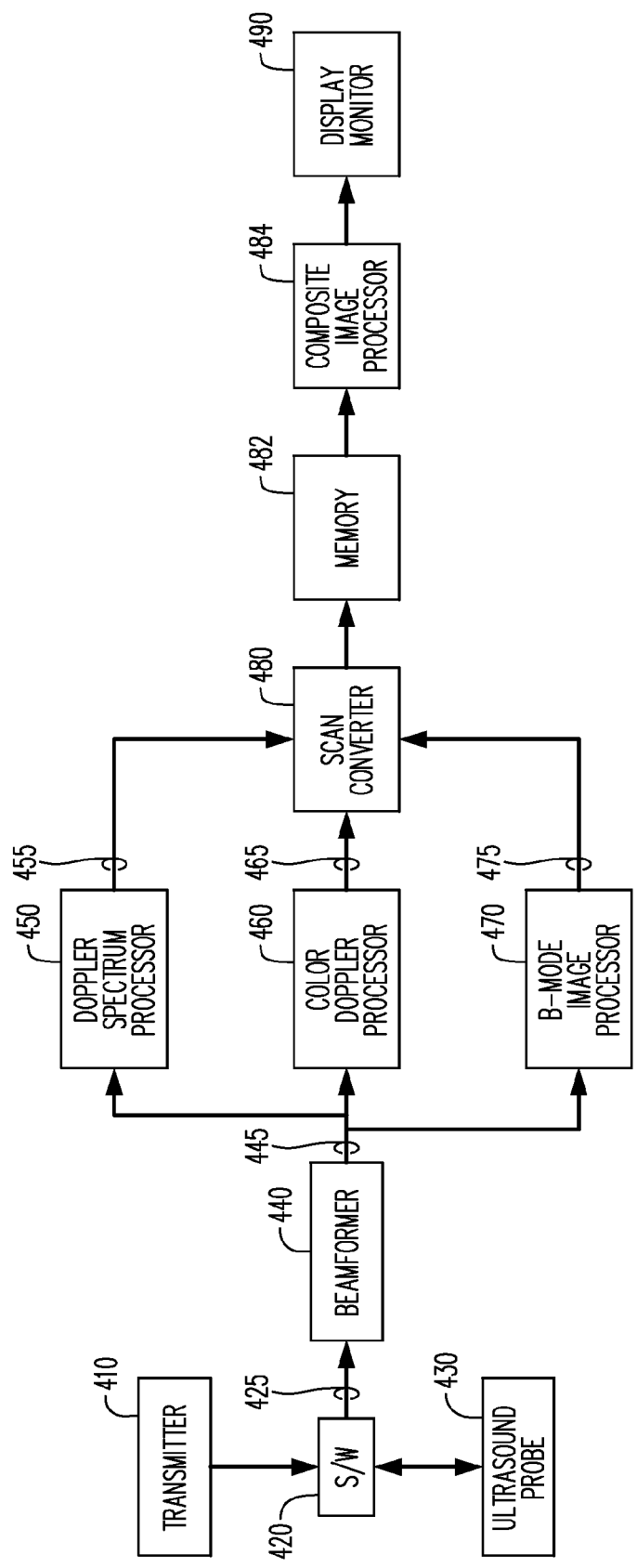
FIG. 4. A diagram of ultrasound imaging system including a composite image processor according to some embodiments.

FIG. 4 shows a diagram of an ultrasound imaging system of the present invention including a composite image processor 484 for improved imaging, such as, but not limited to, improved visualization of interventional devices such as biopsy needles.

The transmitter 410 may contain a transmit beamformer which may apply time delays to signals for transducer elements for focusing and beam steering. For example, a first set of transmit time delays are either generated or read from memory and loaded to a transmit delay table, and a first set of receive time delays/phases are generated or read from memory and loaded to a receive delay table. A first ultrasound image is then acquired at a first beam steering angle. Next, a second set of transmit time delays are either generated or read from memory and loaded to the transmit delay table and a second set of receive time delays/phases are generated or read from memory and loaded to the receive delay table. A second ultrasound image is then acquired at a second beam steering angle. This process continues multiple times as the transmit beamformer and the receive beamformer update each of the delay tables and multiple ultrasound images are acquired at multiple beam steering angles.

Figure 5:
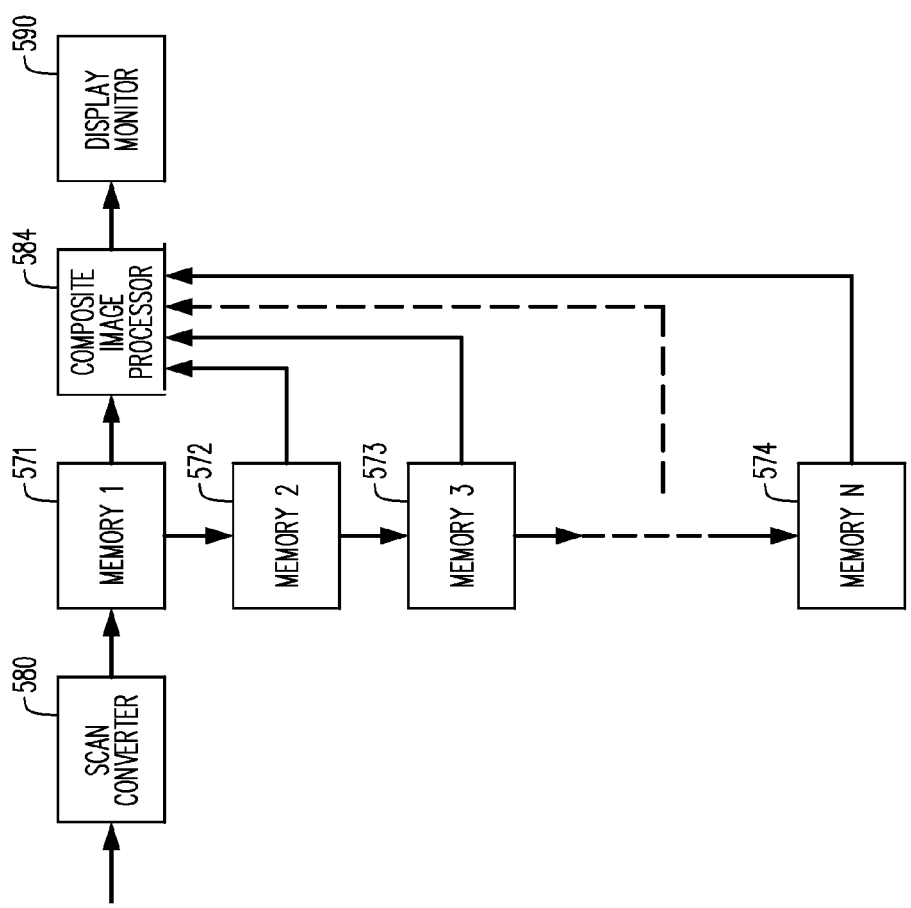
FIG. 5. A diagram of a composite image processor and memories.

From the multiple B-mode ultrasound images stored in memory 482 in FIG. 4, or Memory 1 (571), Memory 2 (572), Memory 3 (573), . . . Memory N (574) as shown in FIG. 5, the composite image processor 484 identifies a value for each image pixel location as described above. The composite image processor 484 may also combine the identified value with a value of the image pixel location of a B-mode ultrasound image acquired at a zero degree beam steering angle or a small beam steering angle, using weights as described above. The resulting image, consisting of a single image pixel value for each of a plurality of image pixel locations, is output to the display monitor 490

The composite image processor 484 may be comprised of general purpose central processing units (CPUs), digital signal processors (DSPs), field programmable Arrays (FPGAs), graphic processing units (GPUs) and/or discreet electronic devices.

FIG. 4 represents a logical architecture according to some embodiments, and actual implementations may include more or different elements arranged in other manners. Other topologies may be used in conjunction with other embodiments. Moreover, each element of the FIG. 4 system may be implemented by any number of computing devices in communication with one another via any number of other public and/or private networks. Two or more of such computing devices may be located remote from one another and may communicate with one another via any known manner of network(s) and/or a dedicated connection. The system may comprise any number of hardware and/or software elements suitable to provide the functions described herein as well as any other functions. For example, any computing device used in an implementation of the FIG. 4 system may include a processor to execute program code such that the computing device operates as described herein.

All systems and processes discussed herein may be embodied in program code stored on one or more non-transitory computer-readable media. Such media may include, for example, a floppy disk, a CD-ROM, a DVD-ROM, a Blu-ray disk, a Flash drive, magnetic tape, and solid state Random Access Memory (RAM) or Read Only Memory (ROM) storage units. Embodiments are therefore not limited to any specific combination of hardware and software.

One or more embodiments have been described. Nevertheless, various modifications will be apparent to those in the art.

The invention claimed is:

1. A method of creating an ultrasound image, comprising;
    creating a plurality of ultrasound images of an area, each of the plurality of ultrasound images acquired using a respective beam steering angle;
    for each of a plurality of image pixel locations in each of the plurality of ultrasound images, determining a value of an image pixel located at an image pixel location;
    for each of the plurality of image pixel locations, identifying a value among the plurality of values determined for the pixel location other than the largest value of the plurality of values determined for the pixel location;
    creating a first output image in which each of the plurality of image pixel locations of the output image includes an image pixel having the value identified for the image pixel location;
    acquiring a second ultrasound image of the area using a beam steering angle substantially perpendicular to an ultrasound transducer array;
    for each of the plurality of image pixel locations in the second ultrasound image, determining a value of an image pixel located at the image pixel location; and
    creating a second output image in which a value of an image pixel located at each of the plurality of image pixel locations of the second output image is the sum of the value identified for the image pixel location in the first output image multiplied by a first weight, and a weighted value of the image pixel determined for the image pixel location in the second ultrasound image multiplied by a second weight.

2. A method according to claim 1, wherein the first weight and the second weight are determined based on image pixel values of the first output image and the second image at the image pixel location.

3. A method according to claim 1, wherein creating the plurality of ultrasound images of an area comprises varying a beam steering angle at a fixed angular increment or at a variable angular increment.

4. A method according to claim 1, wherein the respective beam steering angle is selected from a set of beam steering angles.

5. A non-transitory medium storing processor-executable program code, the program code executable by a device to:
    create a plurality of ultrasound images of an area, each of the plurality of ultrasound images acquired using a respective beam steering angle;
    for each of a plurality of image pixel locations in each of the plurality of ultrasound images, determine a value of an image pixel located at an image pixel location;
    for each of the plurality of image pixel locations, identify a value among the plurality of values determined for the pixel location other than the largest value of the plurality of values determined for the pixel location; and
    create a first output image in which each of the plurality of image pixel locations of the output image includes an image pixel having the value identified for the image pixel location;
    acquire a second ultrasound image of the area using a beam steering angle substantially perpendicular to an ultrasound transducer array
    for each of the plurality of image pixel locations in the second ultrasound image, determine a value of an image pixel located at the image pixel location; and
    create a second output image in which a value of an image pixel located at each of the plurality of image pixel locations of the second output image is the sum of the value identified for the image pixel location in the first output image multiplied by a first weight, and a weighted value of the image pixel determined for the image pixel location in the second ultrasound image multiplied by a second weight.

6. A medium according to claim 5, wherein the first weight and the second weight are determined based on image pixel values of the first output image and the second image at the image pixel location.

7. A medium according to claim 5, wherein creating the plurality of ultrasound images of an area comprises varying a beam steering angle at a fixed angular increment or at a variable angular increment.

8. A medium according to claim 5, wherein the respective beam steering angle is selected from a set of beam steering angle.

9. A system comprising:
an ultrasound transducer comprising an array of transducer elements;
a memory storing processor-executable program code; and
a processor to execute the processor-executable program code in order to cause the system to:
create a plurality of ultrasound images of an area, each of the plurality of ultrasound images acquired using a respective beam steering angle;
for each of a plurality of image pixel locations in each of the plurality of ultrasound images, determine a value of an image pixel located at an image pixel location;
for each of the plurality of image pixel locations, identify a value among the plurality of values determined for the pixel location other than the largest value of the plurality of values determined for the pixel location; and
create a first output image in which each of the plurality of image pixel locations of the output image includes an image pixel having the value identified for the image pixel location;
acquire a second ultrasound image of the area using a beam steering angle substantially perpendicular to an ultrasound transducer array
for each of the plurality of image pixel locations in the second ultrasound image, determine a value of an image pixel located at the image pixel location; and
create a second output image in which a value of an image pixel located at each of the plurality of image pixel locations of the second output image is the sum of the value identified for the image pixel location in the first output image multiplied by a first weight, and a weighted value of the image pixel determined for the image pixel location in the second ultrasound image multiplied by a second weight.

10. A system according to claim 9, wherein the first weight and the second weight are determined based on image pixel values of the first output image and the second image at the image pixel location.

11. A system according to claim 9, wherein creating the plurality of ultrasound images of an area comprises varying a beam steering angle at a fixed angular increment or at a variable angular increment.

12. A system according to claim 9, wherein the respective beam steering angle is selected from a set of beam steering angles.

* * * * *